US006818780B2

(12) United States Patent
Barrera et al.

(10) Patent No.: US 6,818,780 B2
(45) Date of Patent: Nov. 16, 2004

(54) P-HYDROXYPHENYL PROPIONIC ACID DERIVATIVES AS ANTIPROLIFERATIVE AGENTS

(75) Inventors: Jaime Bermejo Barrera, La Laguna (ES); Margarita Hernández Silva, La Laguna (ES); Melchor Álvarez De Mon, Madrid (ES); Juan Pablo Pivel Ranieri, Xativa (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 10/251,914

(22) Filed: Sep. 20, 2002

(65) Prior Publication Data

US 2003/0199575 A1 Oct. 23, 2003

Related U.S. Application Data

(63) Continuation of application No. PCT/ES01/00102, filed on Mar. 16, 2001.

(30) Foreign Application Priority Data

Mar. 20, 2000 (ES) .......................... 200000660

(51) Int. Cl.$^7$ .......................... C07D 307/12
(52) U.S. Cl. ................................ 549/323
(58) Field of Search ........................ 549/323

(56) References Cited

PUBLICATIONS

Gonzalez et al, "Synthesis and Antiproliferation, etc" J.Med-.Chem, 2002, 45, 2558–2361.*

Ogmundsdottir, et al., Anti–proliferative effects of lichen–derived inhibitors of 5–Lipoxygenase on malignant cell–lines and mitogen–stimulated lymphocytes. J. Pharm Pharmacol. 1998, 50:107–115.

Howie, et al., Potential antitumor agents[1a] Synethesis of bifunctional α– methylene –Y– butyrolactones[1b]., J. Med. Chem., 1976, 19:309–313.

Nakagawa, et al., Terrecyclic acid A, A new antibiotic from Adpergillus Terreus. I. Taxonomy, production, and chemical and biological properties. J. Antibiotic, 1982, 35:778–782.

Kupchan, et al., Tumor inhibitos, Structure cytotoxicity relationships among the sesquiterpene lactones., J. Medical Chem., 1971, 14:1147–1152.

Terapéutica farmacologica del dolor. Jesús Flores 1993. Ed. EUNSA. Pamplona 1993. Colección clínica de la salid. Capitulo 5 pp. 145–149.

Abbas AK, Lichtman AH, Pober JS. Cellular and Molecular Immunology. 2$^{nd}$ Ed. W.B.USA: Sanders Company, 1994: Table of Contents plus 31–2.

Metezeau PH, Ronot X, Le Loan–Merliquac Q. Ratinard MH. La Citometrie en Flux. In: Le Gorge Cellulaire. Paris: MEDSI/McGraw Hill, 1988; 77–80.

Balter M, Cohen J. International AIDS Meeting Infects a dose of realism. Science (New Fows) 1998; 281; 159–60.

Mann JM, Tarantola DJ. HIV 1998: the global picture. Sci AM 1998; 279 (1) 82–3.

Bartlett JG, Moore RD. Improving HIV therapy. Sci Am 1988: 279(1); 60–68.

Gleichmann, E., Kimber I Purchase IFH. Immunotoxicology: Suppressive and stimulatory effect of drugs and environmental chemicals on the immune system. Arch Toxicol 1989; 63: 257–73.

Luqmani R, Gordon C; Bacon P. Clinical Pharmacology and modificator of autoimmunity and inflammatorion in rheumatoid disease. Drugs 1994; 47(2): 259–83 Drugs autoimmune diabetes.

Riestra Moriegue JL, Guerro Silva R, Fernandez Sánchez JA, Balio Hernández J, Rodriguez Pérez A, Revisión de los immunesupresores en el tratamiento de la artritis reumatoide. Inflamación 1993; IV (6) 368–81.

Werner GF, Jolle's P. Immunostimulating agents; what next? A review of their present and potential medical applications. Eur J Biochem. 1996; 242: 1–19.

Hernández Silva H. Aportación a la fitoquimica de helechos. Síntesis y funcionalización de una nueva molécula natural bioactiva. Conclusion of Ph.D. Thesis, Universidad de La Laguna (1996).

Kupchan SM, Eakin MA, Thomas AM. Tumour inhibitors. 69. Structure–Cytotoxicity relaitonships among the sequiterpene lactones. J Med Chem 1971; 14(12): 1147–52.

Nakagawa M, Hirota A, Sakai H., Isogai A. Terrecyclic acid A, a new antibiotic from *Aspergillus terreus*. I. Taxonomy, production, and chemical and biological properties. J Antibiot 1982; 35:778–82.

Lebot V, Levesque J. El Kava ¿ un remedio contra el estrés?. Mundo Cientifico 1987; 1978: 366–70.

Jappe V, Framke I, Reinhold D, Gollmick H Sebotropia drug reaction resventing from kava–kava extract therapy. A new entity? J Am Acad Dermatoloyg 1988; 38(1): 104–6.

Morgan DO. Principles of CDK regulation. Nature 1995; 374:131–4.

Edgar BA, Lehner CA. Developmental control of cell cycle regulators: A fly's perspective. Science 1996; 374: 1646–51.

Gray N. Wodicka L, Thunnissen A, Norman T, Kwon S, Espinoza FH et al., Exploiting chemical libraries, structure and genomics in the search for kinase inhibitors. Science 1998; 281:533–8.

(List continued on next page.)

Primary Examiner—Patricia L. Morris
(74) Attorney, Agent, or Firm—Klauber & Jackson

(57) ABSTRACT

Derivatives of the compound p-hydroxyphenyl propionic acid characterised by those derivatives having the general formulas (I) and (Ia), where n can take the values 1,2,3; R can be H or $CH_3$ and $R_1$ can be $CH_3$ or H with pharmacological activity and their application in medicine for the treatment of disorders of the immunological system.

1 Claim, 6 Drawing Sheets

OTHER PUBLICATIONS

Figure 1:
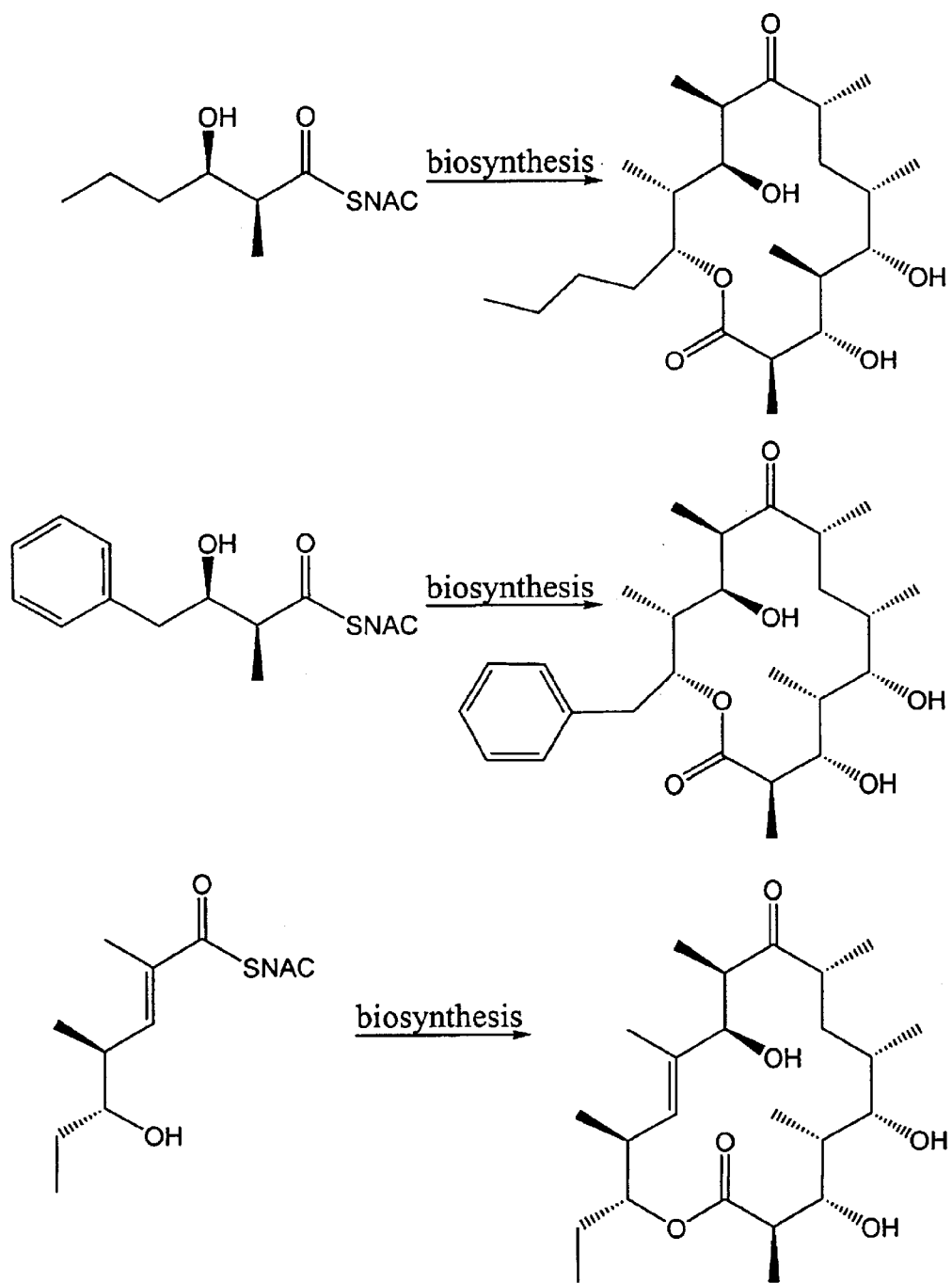
Figure 2:
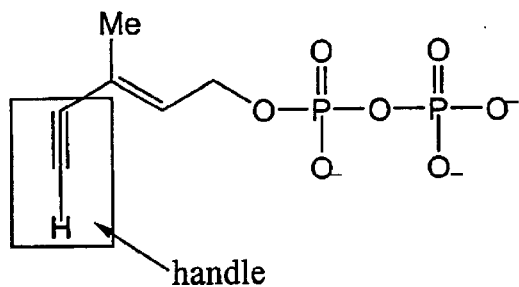
Figure 2:
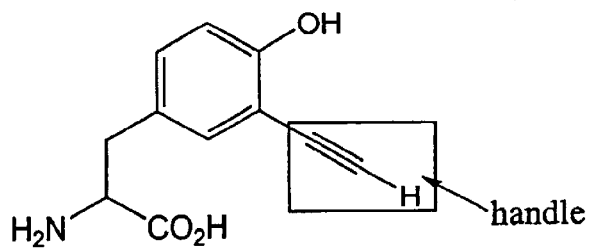
Figure 2:
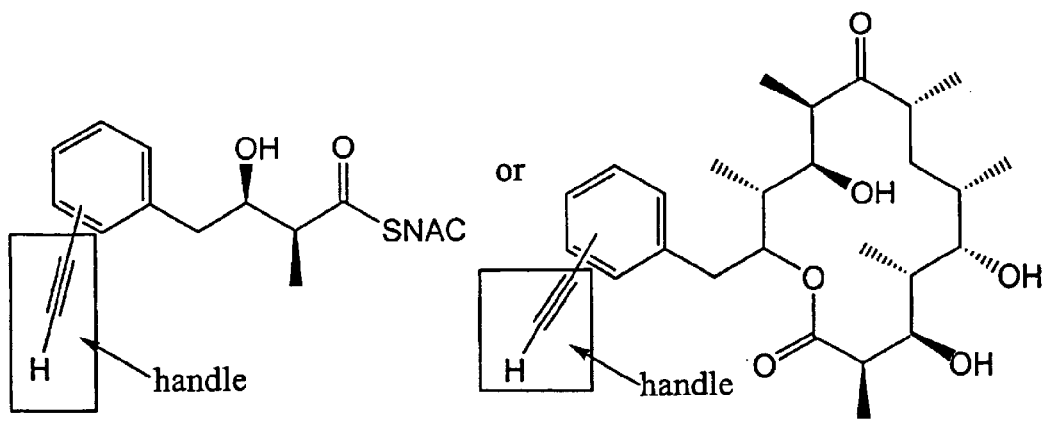
Figure 3:
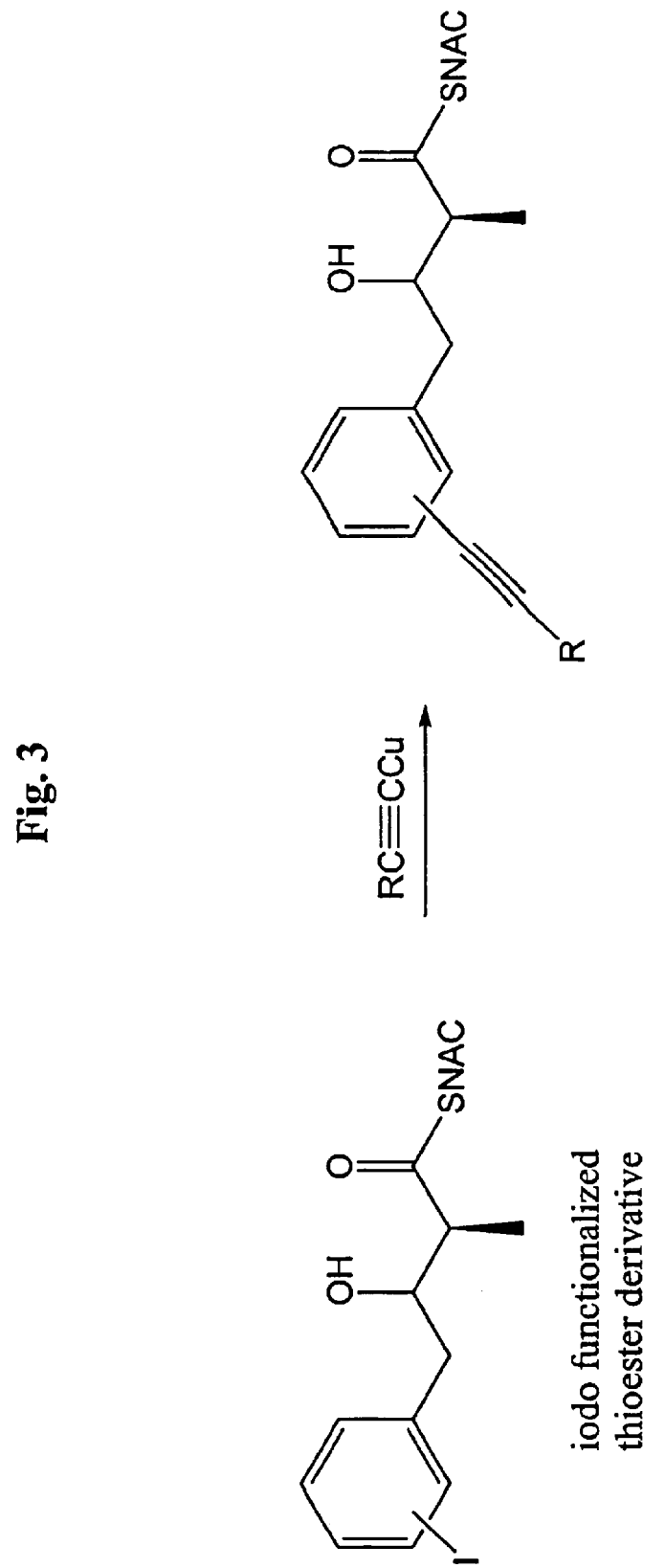
Figure 4:
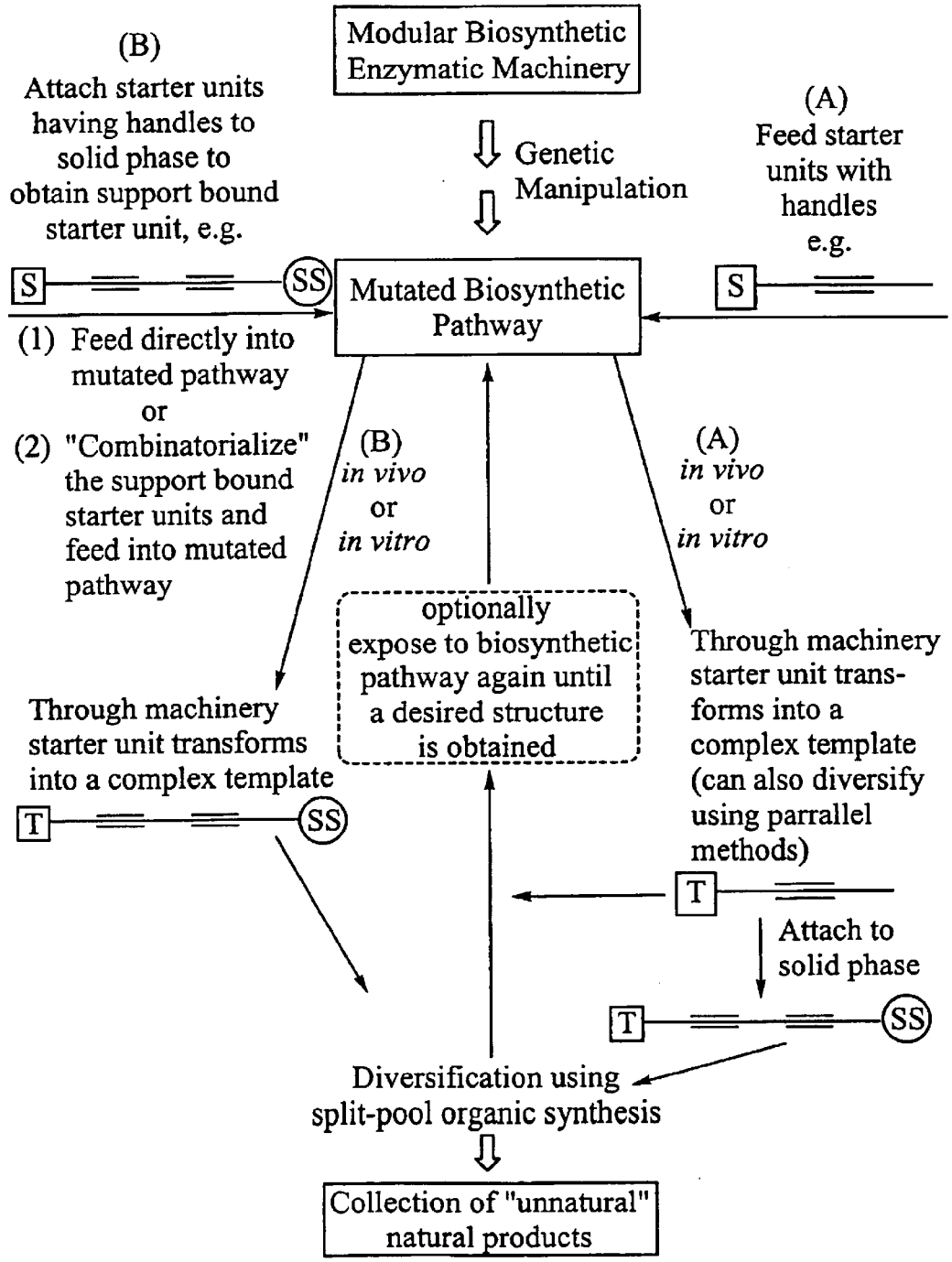
Figure 5A:
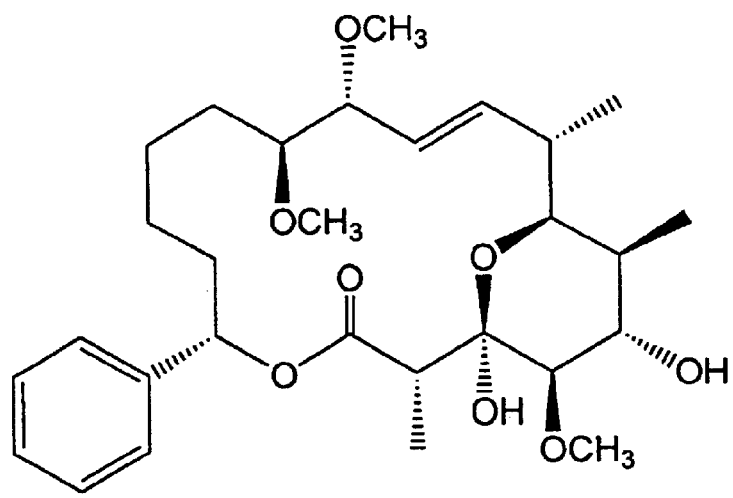
Figure 5B:
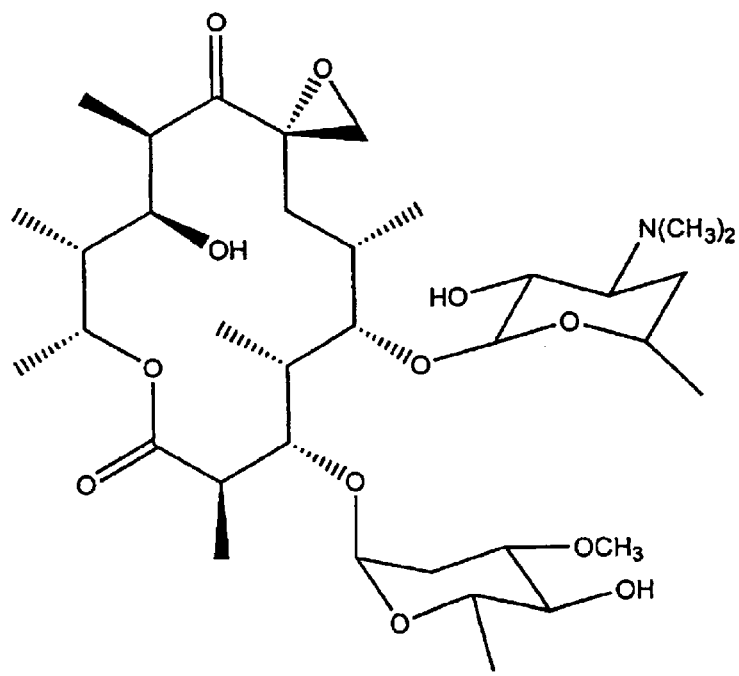
Figure 5C:
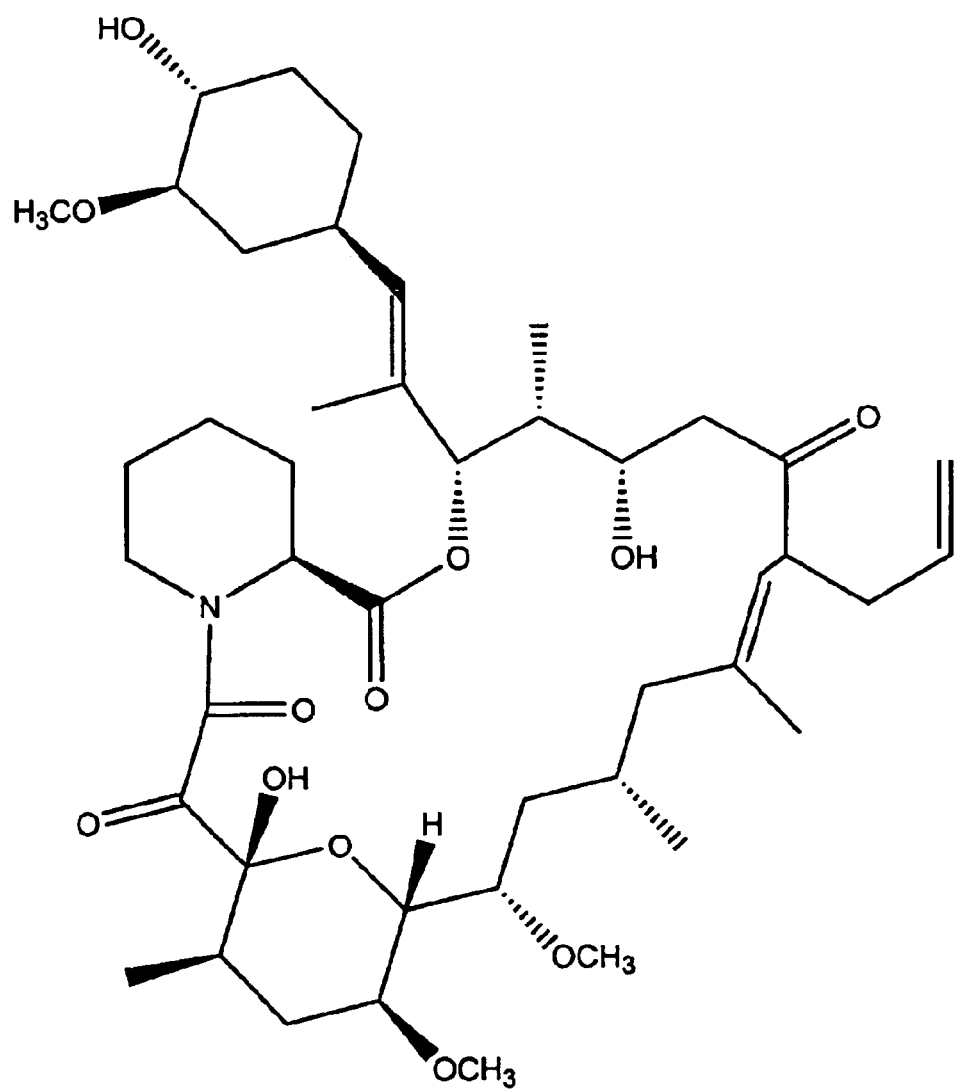

GarUti L, Roberti M, Rossi T, Castelli M, Malagolis M. Synthesis and antiproliferative activity of 3–substituted 1H indole [3,2–d]–1,2,3–triazin–4(3H)–ones. Eur J Med Chem 1993; 33:43–6.

Serrano A, Palacios C, Roy G, Crespón C, Villar M, Nocito M et al. Derivatives of gallic acid induce apoptosis in tumoral cell lines and inhibit lymphocyte proliferation. Arch Bioch Biophysicos 1998; 330(1):49–54.

Saltiel AR, Samyer TK. Targeting signal transduction i the discovery of antiproliferative drugs. Chem and Biology 1996; 3(11):887–93.

Labit–Le–Bouteiller C, Jamme MF, David M, Silve S, Lanau C, Dhers C et al. Antiproliferative effects of SR31747A in animal cell linies are mediated by inhibition of cholesterol biosynthesis at the sterol isomerase step. Dur J Biochem 1998; 256:342–49.

Dell CP. Antiproliferative naphthopyrans: biological activity, mechanistic studies and therapeutic potential. Current Medicinal chemistry 1998; 5:179–94.

Kamei H, Koide T, Kojima T, Hashimoto Y, Hasegawa M. Inhibition of cell growth in cultures by quinones. Cancer Biotherapy & Radiopharmaceuticals 1998; 13(3): 185–188.

Zafra–Polo MC, Figadere B, Gallardo T, Tormo JR, Cortes D. Natural acetogenins from annonaceae, synthesis and mechanism of action. Phytochemistry 1998; 48(7)1087–117.

Cheviron N, Grillon C, Carlier MF, Wdzieczak–Bakala J. The antiproliferative activity of the tetrapeptide acetyl–N–SerAspLysPro, an inhibitor of haematopoiectic stem cell proliferation, is not mediated by a thymosin β4–like effect on actin assembly. Cell Prolif 1996; 29: 437–46.

Gonzalez, Antonio G., et al., A contribution to the phytochemistry of the pteridological flora of the Canary Islands, Recent Res. Devel. In Phytochem., 1 (1997) 411–426.

Basavaiah, D., et al., The Baylis–Hillman Reaction: A Novel Carbon–Carbon Bond Forming Reaction,Pergamon, Tetrahedron, vol. 52, No. 24; 8001–8062.

Loffler, A., et al, Préparation des α–methylène buyyrolactones par réaction de Rèformatsky; synthèse de l'acide protolichéstérinique, Chimia, 23, 1969; 413–416.

Kupchan, SM, et al, Reactions of Alpha Methylene Lactone Tumor Inhibitors with Model Biological Nucleophiles, Science, vol. 168, 376–377.

Hanson, Ronald L. et al, Inhibition of Phosphofructokinase by Quinone Methide and α–Methylene Lactone Tumor Inhibitors, Science, vol. 168, 378–380.

Corey, EJ, et al., Pyridinium Chlorochromate. An Efficient Reagent For Oxidation Of Primary And Secondary Alcohols To Carbonyl Compounds, Tetrahedron Letters No. 31; 1975; 2647–2650.

Nokami, J. et al., Facile Synthesis of 2–Methylene–4–Butyrolactones[1], Chemistry Letters; 1986; 541–544.

Hoffman, HMR., et al., 1,4–Diazobicyclo[2.2.2]octane–Catalyzed Coupling of Aldehydes and Activated Double Bonds[1], Helvetica Chimica Acta—vol. 67, Fasc.2; 1984; 413–415.

* cited by examiner

1) Terpene-based pathway

2) Amino acid-based pathway

3) Polyketide pathway

Combinatorial Biology

Soraphen (A)

Oleandomycin

FK506

P-HYDROXYPHENYL PROPIONIC ACID DERIVATIVES AS ANTIPROLIFERATIVE AGENTS

This application is a continuation of international application number PCT ES01/00102, filed Mar. 16, 2001.

FIELD OF THE TECHNIQUE

Within the therapeutic group of non-steriod antiinflammatories propionic acid derivatives occupy an outstanding place from both the therapeutic and commercial points of view.

Within this subgroup we can distinguish first of all ibuprofen (1), which was the first of a series in which we can today find naproxen (2), ketoprofen (3) and fenbufen (4) among others.

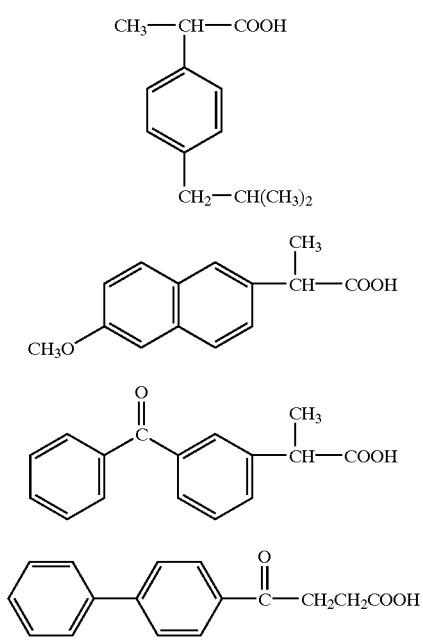

The pharmacodynamic characteristics of all these products is similar, which they present in varying degrees of antiinflammatory, antithermic, analgesic and antiplatlet activity, all of them being non-selective inhibitors of ciclooxygenases (Cox I y Cox II) (*Terapéutica farmacológica del dolor. Jesús Flores* 1993. Ed. EUNSA. Pamplona 1993. Colección clínica de la salud. Capitulo 5, pag: 121–156.).

The structural analogy between compounds (I) and (VI) (the latter being originally found and described from a fern "*Asplenium onopteris*") has led us to a pharmacological study of the two series of functionalised molecules starting from

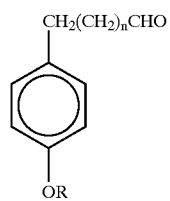

n = 1, 2, 3
R = CH₃, H

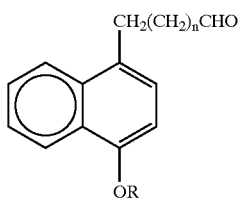

in accordance with that shown in diagrams 1 and 2.

The central idea of the present invention therefore consists of obtaining a series of molecules on the basis of an adequate functionalisation using compound VI of Diagram 1 and using the corresponding derivatives of the aromatic rings, benzene and naphthalene, as functionalised syntones.

ANTECEDENTS OF THE INVENTION

The cell, the structural and functional unit of all living beings, is governed by a series of mechanisms that take decisions which in turn determine different conducts: proliferation, differentiation, activation, senescence and apoptosis. In higher organisms, there are some tissues in which there exist stem cells that generate the functional mature cells by proliferation and differentiation.

Within the systems of higher organisms, the immunological system constitutes an essential defence mechanism for preserving the viability of the individual. Multicellular beings, including humans, find themselves in an environment with a great many microorganisms that can penetrate into their interior and use them for their own growth. The immune system is capable of recognising microorganisms and triggering an effector response leading to their destruction or functional cancellation. Moreover, multicellular beings undergo errors in cell proliferation processes and they accumulate mutations that lead to the tumoral transformation of some of their components. The immune system is also capable of recognising cells that have undergone neoplastic transformation and of successfully suppressing tumoral growth and dissemination. Nevertheless, the effector capacity of the immune system can provoke inflammatory tissue alterations with lesions to parenchymatous components. These processes are accompanied by infiltration and proliferation of cells from the immune system into the tissues. Some originate in the response to infectious agents and can be acute and systemic, such as sepsis and multiorganic inflammatory response, or they can be chronic and localised such as hepatitis, tubercular arthritis, etc. Other inflammatory processes mediated by the immune system are those known as autoimmune, which are triggered in the presence of the actual components of the organism, such as rheumatoid arthritis, inflammatory disease of the digestive tract, etc. As a cellular system, the immune system can also undergo tumoral transformations giving rise to malign lymphoproliferative syndromes. The immune system can also participate in aptogenis of tissue damage by chronic processes such as some demencias and arteriosclerosis.

In the analysis of immunological responses, a distinction is drawn between natural or non-specific immunity and acquired or specific immunity. The latter is in turn divided into tumoral immunity characterised by the production of antibodies by type B lymphocytes and in cell mediation response via T lymphocytes. The immunological response consists of a complex feedback network in which autocrine and paracrine mediators, cytokins, growth factors, etc., all play a role, in addition to the mediators responsible for connection with the endocrine system and the nervous system.

An essential element in the generation of the specific immunological response is the capacity to expand lymphocyte subpopulations by antigen stimulus determined via a complex process of recognition and processing of the antigen followed by a process of presentation to the effector cell that finally generates the response. This process can be summarised by saying that the proliferation of the subpopulations corresponding to the antigen is the essential property of mature lymphocytes (Assas A K, Lichtman A H, Pober J S. Cellular and Molecular Immunology. 2nd ed. W. B. USA: Sanders Company, 1994:31-3).

The cellular mechanisms for proliferation in turn imply a complex mechanism for the reception of signals external to the cell via membrane receptors, and the transmission of those signals to the cell nucleus in order to put into operation the mitotic mechanisms which likewise imply nuclear and cytoplasmatic processes (Metezeau P H, Ronot X, Le Loan-Merliquac Q, Ratinard M H. La Citometrie en Flux. In: Le Gorde Cellulaire. Paris: MEDSI/Mc Gram Hin, 1988:77–87).

The physiological mechanisms of the immunological system must necessarily include an availability of "defensive" cells at sites where their activity is needed, hence the existence of "call" mechanisms, circulation, recruitment and adhesion.

The efficiency of the immunological system is nevertheless subject to dysfunctions which can in general terms be separated into three fundamental types, as has been stated previously. Proliferative dysfunction, that in which a cell population or subpopulation proliferates out of control, giving rise to various types of leukaemias and lymphomas and other malign and benign lymphoproliferative syndromes. Functional dysfunction therefore implies an exacerbation of the response that gives to, for example, autoimmune pathologies due to errors in antigen recognition, or a decrease in the type of response giving rise to different situations of immunosuppression. One particular case consists of pathologies or situations of inflammation (chronic or acute) with the concomitant tissue destruction and functional alteration, which can be produced in the context of systemic autoimmune diseases or specific organs as well as in response to various infectious agents.

The pathology of the immunological system is in some aspects, and paradoxically so, parallel to the course of technological and social processes. For example, there can be no doubting the close relation between the development of the AIDS pandemic with social factors such as the enormous increase in displacements, the liberalisation of customs or the unemployment situation with its consequences of margination and drug addiction (Baiter M, Cohen J. International AIDs Meeting Infects a dose of realism. Science (New Fows) 1998;281:159–60., Mann J M, Tarantola D J. HIV 1998: the global picture. Sci Am 1998;279(1):82–3., Bartlett J G, Moore R D. Improving HIV therapy. Sci Am 1998;279(1):84–7).

Another important factor of immunological pathology is the development of the chemical industry and environmental contamination which propitiates the development of allergies and immunotoxicity (Descotes J. Immunotoxicology of drugs and chemicals. Elsevier Press, 1990., Herchman E, Kimber I, Purches IFH. Immunotoxicology: Suppressive and stimulatory effect of drugs and environmental chemicals on the immune system. Arch Toxicol 1989;63:257–73).

Finally, we can mention that, at least in developed countries, the increase in life expectancy, changes in nutrition, modifications to interactions with infectious agents, the present-day life-style, have all been associated with a greater incidence and prevalence of autoimmune disease and autoimmunity with inadequate recognition of tissues, which are seen as "not one's own", as in rheumatoid arthritis (Lugmano R, Gordon C; Bacon P. Clinical Pharmacology and modificator of autoimmunity and inflammatorion in rheumatoid disease. Drugs 1994;47(2):259–83), autoimmune diabetes (Riestra Moriegue J L, Guerro Silva R, Fernandez Sánchez J A, Balio Hernández J, Rodriguez Pérez A. Revisión de los immunesupresores en el tratamiento de la artritis reumatoide. Inflamación 1993;IV (6):368–81), etc.

Finally, among the aspects tied to technological and environmental development, we can mention the repercussions of exposure to ionising radiations.

Knowledge of the immunological mechanisms and the growing social repercussions of immunological pathologies have, in the last 30 years, led to the development of substances capable of therapeutically manipulating the immunological system (immunomodulators).

In short, we have to understand that immunological dysfunction is always ambivalent and the development of the suppression of some of the functions can occasion the exacerbation of others (and vice versa), and that this implies a special difficulty in the effective therapeutic manipulation of the immunological system.

One of the most surprising pharmacological facts is the structural disparity of the different types of products specifically classified as immunomodulators (Werner G F, Jolle's P. Immunostimulating agents: what next? A review of their present and potential medical applications. Eur J Biochem.1996;242:1–19), even leaving to one side antiinflammatory substances and cytostatic agents (antimitotics).

On the basis of these considerations, there is a clear possibility of designing new active principles provided with pharmacological activity towards the immunological system based on some type of interference with uncontrolled processes of differentiation, activation, proliferation or programmed cell death (apoptosis).

One of the essential aspects already mentioned and to which this present invention is especially tied is the capacity of one type of immune cell, the lymphocytes, to enter into proliferation (mitosis) via different stimuli for which it has specific receptors.

So, one way of blocking this proliferative phenomenon could be to block one or several of the activation mechanisms, i.e., the blocking of specific receptors, to interference with the transmitters of the signal as far as the cell nucleus.

The present invention describes the obtaining of a set of substances capable of interfering with different mechanisms for the transmission of activation signals in immunocompetent cells, thereby blocking processes of cell proliferation.

This will be able to permit the therapeutic use of those substances in processes accompanied by an inadequate proliferation of immune system cells. This implies processes of inflammatory tissue infiltration with lymphocyte proliferation such as what are known as autoimmune diseases and inadequate responses to infectious agents with induction of tissue damage mediated by the immune system, and evidently also including malign and benign lymphoproliferative processes. The lymphocyte proliferation also participates pathogenically in various chronic diseases such as amyloidosis, Alzheimer type demencia, arteriosclerosis, etc., which could benefit from the use of these agents.

The design of such substances starts from the presence of 3-(4-hdroxyphenyl)propionic acid (II) in methanolic extracts of the fern *Asplenium onopteris* (Hernández Silva H. Aportación a la fitoquímica de helechos. Síntesis y funcionalización de una nueva molécula natural bioactiva. Tesis Doctoral, Universidad de La Laguna (1996)). The structural similarity of this molecule to certain non-steriod antiinflammatories led to its use as lead product for its functionalisation and pharmacological evaluation.

There exist antecedents of pharmacological activity of lactones, in particular cytostatic activity of sesquiterpene lactones (Kupchan S M, Eakin M A, Thomas A M. Tumour inhibitors. 69. Structure-cytotoxicity relationships among the sesquiterpene lactones. J Med Chem 1971;14(12):1147–52., 13., Nakagawa M, Hirota A, Sakai H., Isogai A.Terrecyclic acid A, a new antibiotic from Aspergillus terreus. I. Taxonomy, production, and chemical and biological properties. J Antibiot 1982;35:778–82).

Another antecedent consists of lactones derived from kava, a plant used in traditional medicine in Indonesia (Lebot V, Levesque J. El Kava ¿un remedio contra el estrés?. Mundo Científico 1987;178:366–70).

These products are being tested in a wide field of clinical situations such as clinical depressions and myorelaxation, though hepatic and blood toxicity has recently been described for this type of product (Jappe V, Framke I, Reinhold D, Gollmick H Sebotropia drug reaction resventing from kava-kava extract therapy. A new entity? J Am Acad Dermatology 1988; 38(1):104–6).

Antiproliferative products must necessarily act at the level of controlling the cell cycle, which means that it is necessary to have a knowledge of the biochemical mechanisms involved in it. This permits (and will permit) the design of inhibitors with greater safety and specificity (Morgan D O. Principles of CDK regulation. Nature 1995;374:131–4., Edgar B A, Lehner C A. Developmental control of cell cycle regulators: A fly's perspective. Science 1996;374:1646–52).

The outline has very recently been published of the general synthesis of a "library" of protein-kinase inhibitor products with the idea of obtaining therapeutic effects starting from specific blockings of enzyme systems responsible for the progression of the cell cycle (Gray N, Wodicka L, Thunnissen A, Norman T, Kwon S, Espinoza F H et al. Exploiting chemical libraries, structure and genomics in the search for kinase inhibitors. Science 1998; 281:533–8).

Various indole derivatives have recently also recently been discovered (Garoti L, Roberti M, Rossi T, Castelli M, Malagolis M. Synthesis and antiproliferative activity of 3-substituted 1H indole [3,2-d]-1,2,3-triazin-4(3H)-ones. Eur J Med Chem 1993; 33:43–6.) as have those of gallic acid (Serrano A, Palacios C, Roy G, Crespón C, Villar M, Nocito M et al. Derivatives of gallic acid induce apoptosis in tumoral cell lines and inhibit lymphocyte proliferation. Arch Bioch Biophysicos 1998;330(1):49–54.), containing this pharmacological activity, though via different mechanisms.

From everything stated above, it clearly emerges that the maladjustment of the transduction paths for signals controlling cell growth can lead to the development of tumoral pathologies. Consequently, the possibility exists of a design of drugs aimed specifically at blocking the transduction of signals (whether these be of the protein-protein type or of the "cascade phosphylation" type (Saltiel A R, Samyer T K. Targeting signal transduction in the discovery of antiproliferative drugs. Chem and Biology 1996;3(11):887–93). Finally, mention is made of novel antecedents in relation to antiproliferative substances (Babit-Le-Bouteiller C, Jamme M F, David M, Silve S, Lanau C, Dhers C et al. Antiproliferative effects of SR31747A in animal cell lines are mediated by inhibition of cholesterol biosynthesis at the sterol isomerase step. Eur J Biochem 1998;256:342–59., Dell C P. Antiproliferative naphthopyrans: biological activity, mechanistic studies and therapeutic potential. Current Medicinal Chemistry 1998;5:179–94., Kamei H, Koide T, Kojima T, Hashimoto Y, Hasegawa M. Inhibition of cell growth in cultures by quinones. Cancer Biotherapy & Radiopharmaceuticals 1998;13(3):185–188., Zafra-Polo M C, Figadere B, Gallardo T, Tormo J R, Cortes D. Natural acetogenins from annonaceae, synthesis and mechanism of action. Phytochemistry 1998;48(7):1087–117., Cheviron N, Grillon C, Carlier M F, Wdzieczak-Bakala J. The antiproliferative activity of the tetrapectide acetyl-N-SerAspLysPro, an inhibitor of haematopoietic stem cell proliferation, is not mediated by a thymosin □4-like effect on actin assembly. Cell Prolif 1996;29:437–46).

DESCRIPTION OF THE INVENTION

The compounds of the invention have the following chemical structures:

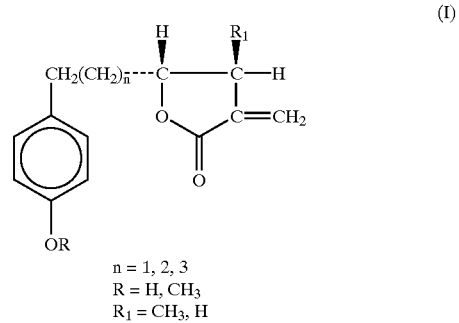

(I)

n = 1, 2, 3
R = H, CH$_3$
R$_1$ = CH$_3$, H

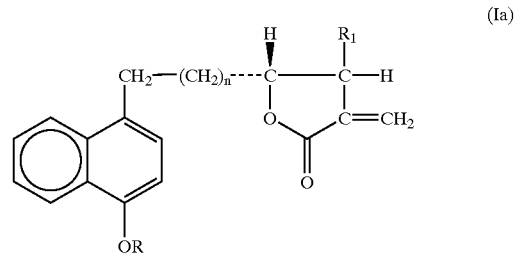

(Ia)

For the purposes of the general description of the invention, we consider the synthesis of the precursor (II) or of that corresponding to the naphthyl series (IIa).

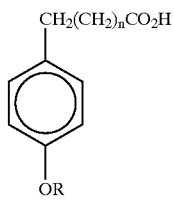
n = 1, 2, 3
R = H, CH₃
(II)
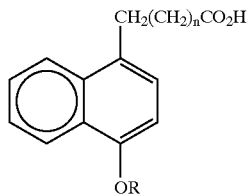
(IIa)
For this we start from the substances (III), (IV) and (V) as per Diagram 1:
Diagram 1
(benzyl series)
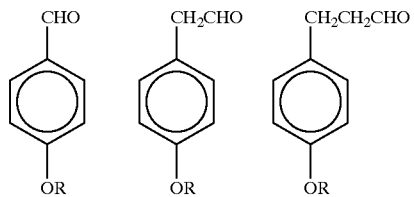
(1) Ac₂O/Py
(2) (CH₃O)₂P(O)CHCO₂CH₃
(52%) (3) H₂/Pd-C
(4) LiAlH₄/THF
(5) CrO₃/H⁺
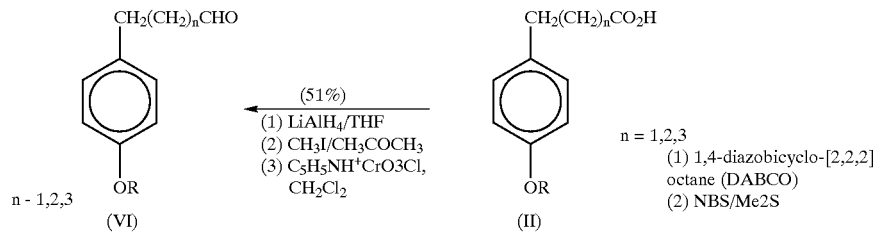
(51%)
(1) LiAlH₄/THF
(2) CH₃I/CH₃COCH₃
(3) C₅H₅NH⁺CrO3Cl, CH₂Cl₂
n = 1,2,3
(1) 1,4-diazobicyclo-[2,2,2] octane (DABCO)
(2) NBS/Me2S
Moreover:
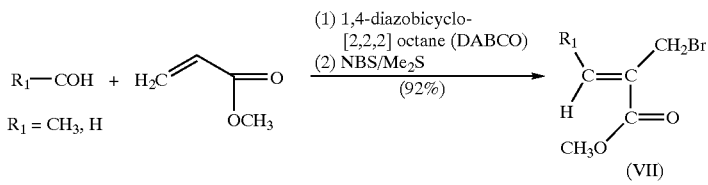
(1) 1,4-diazobicyclo-[2,2,2] octane (DABCO)
(2) NBS/Me2S
(92%)
R₁ = CH₃, H A functionalised allylation of (VI) and (VII) gave us (I)
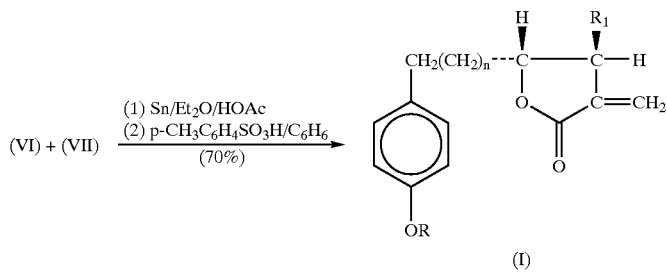
For the "naphthyl" series, see Diagram 2:
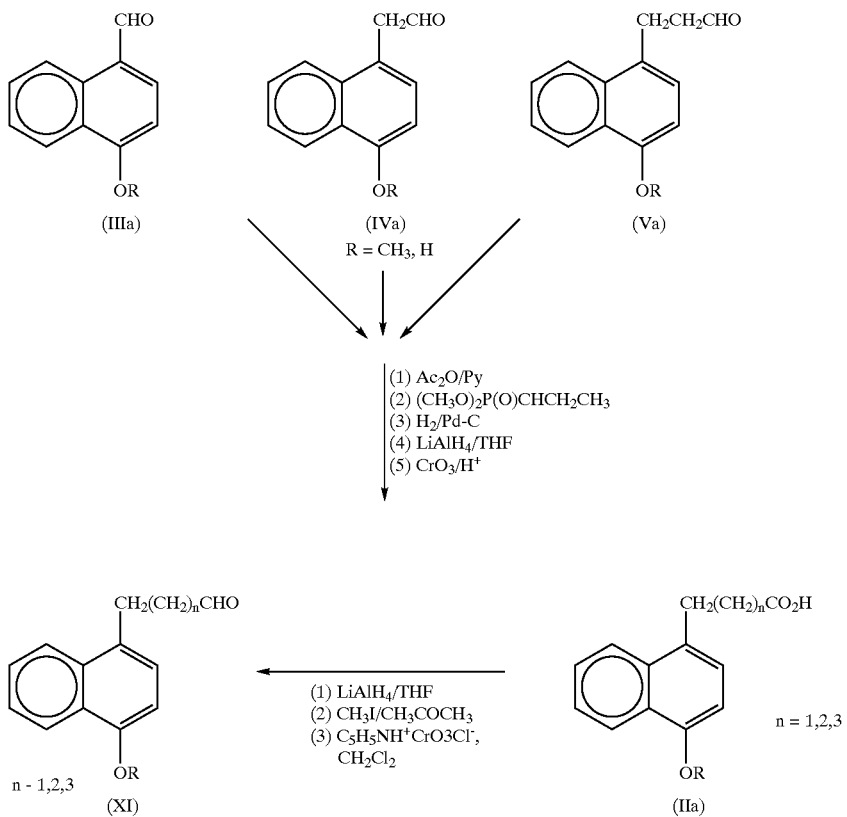
A functionalised allylation of (XI) and (VII) as in the diagram 1 gave us (Ia).
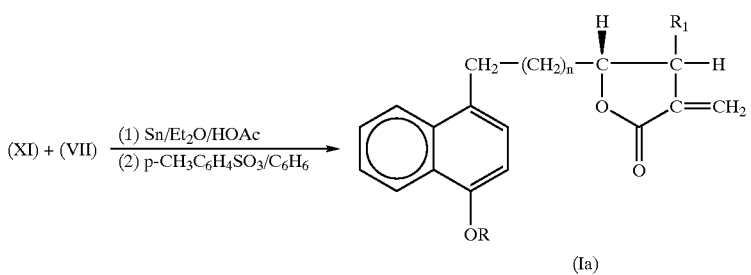

The precursors would be:

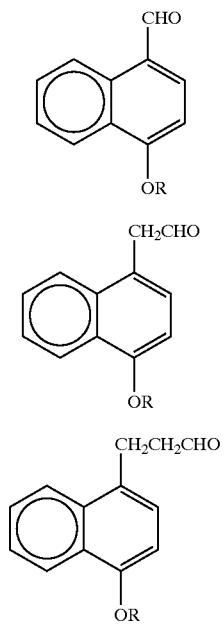

(IIIa)

(IVa)

(Va)

with all the synthesis steps of Diagram 1 being maintained up to the obtaining of the end products. (I), where the product (IIa) is the corresponding precursor of the naphthyl series.

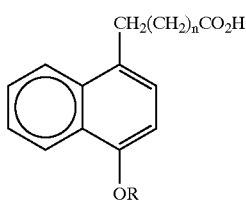

(IIa)

Described below is the synthesis of the product of the invention (I) when n=1, R=R$_1$=CH$_3$; n=1, R=CH$_3$, R$_1$=H.

For this, we have prepared the following compounds:

3-(4-Hydroxyphenyl) propionic acid, having the following structural formula:

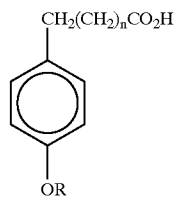

(II)

n = 1
R = H which can be prepared from commercial 4-hydroxybenzaldehyde, of formula:

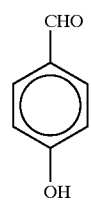

(III)

For the preparation of the acetyl derivative of (III), of formula:

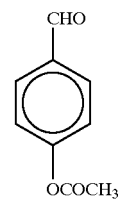

The aldehyde (III) was treated with acetic anhyride [(CH$_3$—CO)$_2$O] and pyridine (C$_5$H$_5$N).

EXAMPLES OF CARRYING OUT THE INVENTION

The invention is explained via the following experiments:
Preparation of 3-(4-hydroxyphenyl) propionic acid
Acetylation of 4-hydroxybenzaldehyde (III)

6.0 g (48.18 mmoles) of (III) were dissolved in 1 ml of pyridine and 2 ml of acetic anhydride were added. The mixture was left to rest at room temperature for 24 h. It was poured onto water (200 ml) and an extraction was performed with diethyl ether (3×100 ml). The ether extracts were washed three times, each time with 100 ml of a solution of dilute hydrochloric acid (0.5 N) and then with sodium bicarbonate. The ether extracts were dried over anhydrous sodium sulphate and vacuum concentrated to give an oil 6.3 g. (100% yield) of 4-acetylbenzaldehyde.

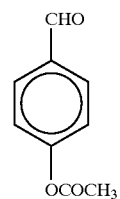

Spectroscopic data.-

| | |
|---|---|
| IR ν$_{max}$(CHCl$_3$) cm$^{-1}$: | 2830, 2743, 1762, 1702, 1601, 1503, 1370, 1300, 1194, 1156, 1013, 911, 860, 830, 781, 711. |
| EM m/z (rel. int.): | 164[M]$^+$ (4), 122[M-42]$^+$ (17), 121[M-43]$^+$ (34), 92(20), 93(14), 65(100). |
| $^1$H RMN (δ, CDCl$_3$): | 2.09(s, 3H, C$\underline{H}_3$CO), 7.05(d, J=8.3Hz, 2H), 7.68(d, J=8.3Hz, 2H), 9.74(s, 1H). |
| $^{13}$C RMN (δ, CDCl$_3$): | 20.84(q), 122.16(d) (intensity for 2CH), 131,42(d) (intensity for 2CH), 155.14(s), 168.56(s), 190.92(s). |

Preparation of the Methyl Ester of 4-acetylcinnamic acid

In a two-neck flask containing 250 ml of dry benzene, 2 g were added of a suspension of sodium hydride (1.19 g, 49.98 mmoles) in an argon atmosphere and at 0° C. Trimethylphosphone acetate was then slowly added (8.24 ml, 49.98 mmoles). When the ilide had formed, 4-acetylbenzaldehyde was added (5.47 g, 33.33 mmoles). At the end of one hour, the reaction was complete and the mixture was poured onto a saturated solution of NaCl. It was extracted three times with diethyl ether and the phases were washed twice with distilled water. It was dried over anhydrous $Na_2SO_4$, filtered and the solvent was removed by distillation. After purification in a column of silica gel, 6.74 g (92% yield) were obtained of a white crystalline product, m.p. 61–62° C.

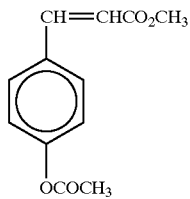

Spectroscopic data.-

| | |
|---|---|
| IR $v_{max}$(CHCl$_3$) cm$^{-1}$: | 1763, 1712, 1637, 1435, 1370, 1204, 1165, 985, 834, 791. |
| EM m/z (rel. int.): | 220[M$^+$] (9), 189[M-OCH$_3$]$^+$ (6), 178[M-OCH$_3$]$^+$ (92), 148[M-72]$^+$ (10), 147[M-CH$_2$CO$_2$CH$_3$]$^+$ (100), 119[M-CO$_2$CH$_3$ + COCH$_3$]$^+$ (22), 91(23), 77(5). |
| $^1$H RMN (δ, CDCl$_3$): | 2.19(s, 3H, —COC$\underline{H}_3$), 3.70(s, 3H, —CO$_2$C$\underline{H}_3$), 6.31(d, J=16Hz, 1H, —C$\underline{H}$=CH—), 7.03(d, J=8.5Hz, 2H), 7.43(d, J=8.6Hz, 2H,), 7.58(d, J=16Hz, 1H, —CH=C$\underline{H}$—). |
| $^{13}$C RMN (δ, CDCl$_3$): | 21.02(q), 51.64(d), 117.83(d), 122.05(d), 129.11(d, intensity for 2CH), 131.98(s), 143.65(d), 151.99(s), 167.21(s), 169.05(s). |

Preparation of the Methyl Ester of 3-(4-acetyl-phenyl) propionic acid 6.70 g (30.45 mmoles) of the methyl ester of 4-acetylcinamic acid were dissolved in 100 ml of ethyl acetate and hydrogenated using 5% Pd/C (1.5 g) as catalyst under $H_2$, for four hours. It was filtered and concentrated to give an oil, 6.17 g (99.2% yield) of methyl ester of 3-(4-acetylphenyl) propionic acid.

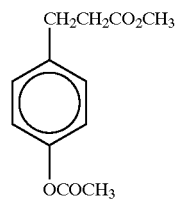

Spectroscopic data.-

| | |
|---|---|
| IR $v_{max}$(CHCl$_3$) cm$^{-1}$: | 3025, 2952, 2852, 1750, 1723, 1602, 1507, 1437, 1369, 1369, 1296, 1228, 1194, 1166, 1102, 913, 849, 638. |
| EM m/z (rel. int.): | 222[M$^+$] (6), 180[M-(CHCO$_2$CH$_3$ + COCH$_3$)]$^+$ (98), 149[M-CH$_2$CO$_2$CH$_3$]$^+$ (10), 107[M-(CHCO$_2$CH$_3$ + COCH$_3$)]$^+$ (100), 91(5), 77(4). |
| $^1$H RMN (δ, CDCl$_3$): | 2.25(s, 3H, COC$\underline{H}_3$), 2.60(t, J=7.6Hz, 2H), 2.29(t, J=7.7Hz, 2H), 3.64(s, 3H, OC$\underline{H}_3$), 6.98(d, J=8.5Hz, 2H), 7.18(d, J=8.5Hz, 2H). |

-continued

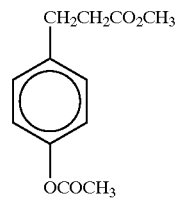

Spectroscopic data.-

| | |
|---|---|
| $^{13}$C RMN (δ, CDCl$_3$): | 20.73(q), 29.96(t), 35.25(t), 121.26(d, intensity for 2CH), 128.96(d, intensity for 2CH), 138(s), 148.99(s), 169.56(s), 173.13(s). |

Preparation de 3-(4-hydroxyphenyl)-1-propanol

To 3.82 g (17.36 mmoles) of methyl ester of 3-(4-acetylphenyl) propionic acid were added 100 ml of dry tetrahydrofurane. To this solution were slowly added 1.80 g (47.43 mmoles) of lithium aluminium hydride (LiAlH$_4$). The reaction mixture was refluxed in an argon atmosphere for 4 hours. At the end of the reaction, water was carefully added, extraction was performed three times with diethyl ether and the result was vacuum dried over anhydrous sodium sulphate, giving 1.70 g (65% yield) of 3-(4-hydroxyphenyl)-1-propanol. Crystallisation in methanol gave a white crystalline solid m,.p.=52–53° C.

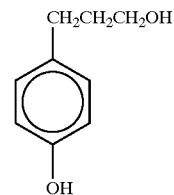

Spectroscopic data.-

| | |
|---|---|
| IR $v_{max}$(CHCl$_3$) cm$^{-1}$: | 3338, 2924, 2853, 1612, 1514, 1460, 1376, 1240, 1037, 824. |
| EM m/z (rel. int.): | 152[M$^+$] (81), 134[M-18]$^+$ (39), 121[M-CH$_2$OH]$^+$ (8), 108[M-C$_2$H$_5$OH]$^+$ (30), 107[M-C$_2$H$_5$O]$^+$ (100), 91(12), 77(7). |
| $^1$H RMN (δ, CDCl$_3$): | 1.87(m, 2H, —C$\underline{H}_2$—), 2.65(t, J=7.5Hz, aryl-C$\underline{H}_2$), 3.69(t, J=6.5Hz, 2H, C$\underline{H}_2$O), 6.76(d, J=8Hz, 2H), 7.06(d, J=8Hz, 2H). |
| $^{13}$C RMN (δ, CDCl$_3$): | 29.68(t), 62.3(t), 115.22(d, intensity for 2CH), 129.45(d, intensity for 2CH), 133.68(s), 153.80(s). |

Preparation of 3-(4-methoxyphenl)-1-propanol 2.26 g (14.87 mmoles) of 3-(4-hydroxyphenyl)-1-propanol were dissolved in dry acetone (20 ml) and potassium carbonate (2.05 g, 14.87 mmoles) was added, followed by methyl iodide (MeI) (2.11 g, 14.87 mmoles). The mixture was kept at reflux in a water bath at 60–70° C. for 48 h. After that period of time, it was diluted with water and the acetone was removed at reduced pressure. Extraction was performed with diethyl ether, and the result was washed with water, dried over sodium sulphate, filtered and the solvent was evaporated in a vacuum to give an oil (2.35 g) (94.93% yield) of 3-(4-methoxyphenyl)-1-propanol.

Spectroscopic data.-

| | |
|---|---|
| IR $v_{max}$ (CHCl$_3$) cm$^{-1}$: | 3360, 2937, 2832, 1604, 1578, 1515, 1460, 1260, 1034, 1030, 835. |
| EM m/z (rel. int.): | 166 [M$^+$] (32), 148 [M-18]$^+$ (15), 135 [M-31]$^+$ (5), 121 [M-C$_2$H$_5$O]$^+$ (100), 107 [M-C$_3$H$_7$O]$^+$ (5), 91 (25). |
| $^1$H RMN (δ, CDCl$_3$): | 1.89 (m, 2H, —CH$_2$—), 2.66 (t, J = 7.8 Hz, 2H, phenyl-CH$_2$—), 3.67 (t, J = 6.5 Hz, —CH$_2$O), 3.80 (s, 3H, phenyl-OCH$_3$), 6.84 (d, J = 8.4 Hz, 2H), 7.13 (d, J = 8.4 Hz, 2H). |
| $^{13}$C RMN (δ, CDCl$_3$): | 30.94 (t), 34.23 (t), 55.04 (q), 61.77 (t), 113.60 (d), 113.68 (d), 129.12 (d), 129.20 (d), 133.80 (s), 157.52 (s). |

Preparation of 3-(4-methoxyphenyl)-propanal 2.34 g (14.10 mmoles) of 3-(4-methoxyphenyl)-1-propanol were dissolved in 20 ml of dry dichloromethane and slowly added to a suspension of 4.56 g (21.15 mmoles) of pyridinium chlorochromate in 25 ml of dichloromethane. Once the reaction was completed, which was followed by thin layer chromatography, 3 ml of diethyl ether were added in portions and the mixture was filtered over celite. The ether phase was washed three times with water and left to dry over anhydrous sodium sulphate for an entire night. The 3-(4-methoxyphenyl)-propanal was purified by column chromatography using as eluent ethyl acetate: dichloromethane in increasing polarity, with 1.20 g of an oil being obtained (52% yield).

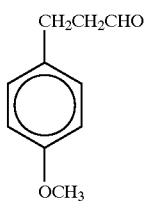

Spectroscopic data.-

| | |
|---|---|
| IR $v_{max}$(CHCl$_3$) cm$^{-1}$: | 2840, 2730, 1716, 1600, 1580, 1511, 1440, 1175, 1109, 1076, 814. |
| EM m/z (rel. int.): | 164[M$^+$] (23), 121(100), 108(30), 91(25), 78(20), 77(16). |
| $^1$H RMN (δ, CDCl$_3$): | 2.70(t, J=7.5Hz, 2H, —CH$_2$—), 2.91 t, J=7.3Hz, 2H, phenyl-CH$_2$—), 3.79 s, 3H, phenyl-OCH$_3$), 6.84(d, J=8.4Hz, 2H), 7.12(d, J=8.4Hz, 2H), 9.60(s, 1H, CHO). |
| $^{13}$C RMN (δ, CDCl$_3$): | 27.11(t), 45.38(t), 55.09(q), 113.75(d), 113.84(d), 129.10(d), 129.15(d), 132.21(s), 157.94(s), 201.72(s). |

Preparation of 3-(4-hydroxyphenyl) propionic acid 0.79 g (5.19 mmoles) of 3-(4-hydroxyphenyl)-1-propanal were dissolved in acetone (20 ml) and Jones reagent (chromic anhydride in sulphuric acid) (8 ml) was added to it drop by drop until the yellow-brown colour persisted. The solution was stirred for one hour at 0° C. The excess reagent was destroyed with methanol and the solution was filtered and evaporated at reduced pressure. The residue was extracted in ethyl acetate, dried over anhydrous sodium sulphate and concentrated, diving an impure residue (0.6470 g), which was chromatographed over silica gel, obtaining 0.545 g (63.1% yield) of 3-(4-hydroxyphenyl) propionic acid. Recrystallisation in methanol gave m.p.=121° C.

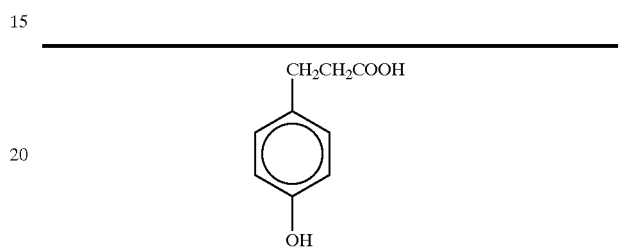

Spectroscopic data.-

| | |
|---|---|
| IR $v_{max}$(CHCl$_3$) cm$^{-1}$: | 3400, 2930, 1702, 1597, 1511, 1460, 1377, 1298, 1222, 1176, 1105, 919, 928, 774, 722. |
| EM m/z (rel. int.): | 166[M$^+$] (46), 107[M-59]$^+$ (100), 91(6), 77(7). |
| $^1$H RMN (δ, CDCl$_3$): | 2.53(t, J=7.5Hz, 2H), 2.80(t, J=7.5Hz, 2H), 6.73(d, J=8.4Hz, 2H), 7.06(d, J=8.4Hz, 2H). |
| $^{13}$C RMN (δ, CDCl$_3$): | 30.57(t), 36.33(t), 115.93(d, intensity for 2CH), 130.03(d, intensity for 2CH), 132.53(s), 156.50(s), 174.18(s). |

Preparation of Methyl 3-hydroxy-2-methylidene-butanoate 8.8 g (0.2 ml, 11.3 moles) of recently distilled acetaldehyde were made to react with 25.83 g (27.0 ml, 0.30 moles) of methyl acrylate and 2.5 g (0.002 moles) of 1,4-diazabicyclo[2,2,2]-octane (DABCO). The mixture was left to react at room temperature with stirring, until all the acetaldehyde had reacted (approximately seven days). At the end of that time, extraction was performed with diethyl ether (2×100 ml) and the result was washed with water (2×400 ml). The ether extracts were dried over anhydrous sodium sulphate and vacuum concentrated, giving 23.4 g (90% yield) of a colourless oil of methyl 3-hydroxy-2-methylidene-butanoate.

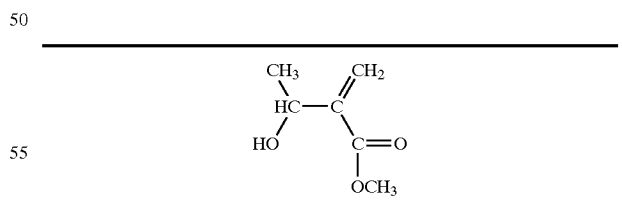

Spectroscopic data.-

| | |
|---|---|
| IR $v_{max}$(CHCl$_3$) cm$^{-1}$: | 3446, 2976, 2855, 1716, 1629, 1438, 1282, 1196, 1163, 1094, 1041, 957, 925, 821. |
| EM m/z (rel. int.): | 130[M$^+$] (1), 115[M-15]$^+$ (74), 112[M-18]$^+$ (8), 99[M-OCH$_3$]$^+$ (25), 98[M-CH$_3$OH]$^+$ (37), 71[M-59(CO$_2$CH$_3$)]$^+$ (32), 55(100). |
| $^1$H RMN (δ, CDCl$_3$): | 1.27(d, J=6.8Hz, 3H, CH$_3$—), 3.26(s wide, 1H, OH), 3.68(s, 3H, CH$_3$O—), 4.55(q, J=6.3Hz, 1H, HC—OH), 5.79(s wide, 1H, CH$_2$=C—), 6.13(s wide, 1H, CH$_2$=C—). |

-continued

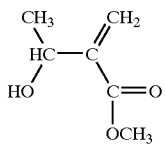

Spectroscopic data.-

| $^{13}$C RMN (δ, CDCl$_3$): | 21.75(q), 51.69(q), 66.63(d), 123.87(t), 143.60(s), 166.91(s). |
|---|---|

Preparation of Methyl 2-bromomethyl-2-butenoate 8.0 g (46 mmoles) of N-bromosuccinimide were dissolved in 60 ml of dry dichloromethane and were cooled to 0° C. To the mixture were added drop by drop 4 ml (50 mmoles) of dimethyl sulphide dissolved in 40 ml of chloromethane. The mixture was stirred for 10 minutes at 0° C. At the end of that time 5.46 (42 mmoles) of a solution of methyl 3-hydroxy-2-methylidene-butanoate in 40 ml of dichloromethane were slowly added to it. The resulting suspension was stirred for 24 hours at room temperature until a transparent solution was obtained. To this mixture was added n-hexane (100 ml) and it was poured into a separating funnel containing 200 ml of a saturated solution of sodium chloride and ice. The organic phase was washed with 100 ml of a saturated solution of sodium chloride. The aqueous phases were extracted with diethyl ether (2×100 ml), they were washed with water (3×100 ml) and they were dried over anhydrous sodium sulphate. They were vacuum concentrated giving 7.45 g (92% yield) of a syrupy liquid of methyl 2-bromomethyl-2-butanoate.

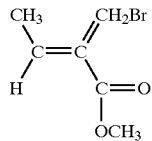

Spectroscopic data.-

| IR $v_{max}$(CHCl$_3$) cm$^{-1}$: | 1715, 1646, 1435, 1284, 1194, 1165, 1083, 1049, 876, 766. |
|---|---|
| EM m/z (rel. int.): | 194(5), 193[M$^+$] (5), 163(7), 161[M-OCH$_3$]$^+$ (6), 135(4), 133[M-CO$_2$CH$_3$]$^+$ (4), 113[M-Br]$^+$ (95), 81(53), 59(97), 53(100). |
| $^1$H RMN (δ, CDCl$_3$): | 1.84(d, J=6.7Hz, 3H, H$_3$CCH=), 3.66(s, 3H, OCH$_3$), 4.14(s, 2H, —CH$_2$Br), 6.97(q, J=7Hz, 1H, HC=H). |
| $^{13}$C RMN (δ, CDCl$_3$): | 14.36(q), 23.78(t), 51.77(q), 129.95(s), 143.04(d), 165.55(s). |

Preparation of 5-[2-(4-methoxyphenyl-ethyl]-4-methyl-3-methylene-dihydrofuran-2-one (I)

To a suspension of metallic tin (1.34 g, 11.30 mmoles) in diethyl ether (22.6 ml) and water (5.65 ml), 2.18 g (11.30 mmoles) of methyl 2-bromomethyl-2-butenoate, 2.04 g (12.44 mmoles) of 3-(4-methoxyphenyl) propanal and sufficient quantities of acetic acid were added with stirring. The mixture was refluxed with stirring for 9 hours at 50° C. At the end of that time, water was added and an extraction was performed with diethyl ether (3×100 ml), it was washed with water and dried over anhydrous sodium sulphate. The result was concentrated obtaining 6.42 g of an oily product which, by means of later treatment with catalytic quantities of p-toluensulphonic acid in benzene at room temperature for 12 h, gave 7.92 g (69.5% yield) of 5-[2-(4-methoxyphenyl-ethyl]-4-methyl-3-methylene -dihydrofuran-2-one [(I), n=1, R=H; R$_1$=CH$_3$] in oil form.

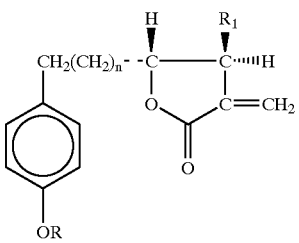

Spectroscopic data.-

| IR $v_{max}$(CHCl$_3$) cm$^{-1}$: | 2938, 2837, 1736, 1663, 1611, 1513, 1456, 1246, 1178, 1124, 1034, 948, 832. |
|---|---|
| EM m/z (rel. int.): | 246[M$^+$] (99), 147[M-(C$_5$H$_7$O)]$^+$ (98), 135[M-(C$_6$H$_7$O$_2$)]$^+$ (19), 134[M-112]$^+$ (29), 121[M-(C$_7$H$_9$O$_2$)]$^+$ (100), 107[M-(C$_8$H$_{11}$O$_2$)]$^+$ (14), 92(29), 91(84). |
| $^1$H RMN (δ, CDCl$_3$): | 1.13(d, J=7Hz, 3H, CH$_3$—), 1.74(t, J=7.8Hz, 2H, CH$_2$), 2.67(m, 2H, O—CH$_2$—), 3.17(deformed quartet, 1H, CH), 3.81(s, 3H, O—OCH$_3$), 4.46(quartet, J=5.8Hz, 1H, HCO), 5.57(d, J=2.5Hz, 1H, =CH$_2$), 6.25(d, J=2.5Hz, 1H, =CH$_2$), 6.88(d, J=8.6Hz, 2H), 7.16(d, J=8.6Hz, 2H). |
| $^{13}$C RMN (δ, CDCl$_3$): | 13.61(q), 30.59(t), 32.64(t), 37.14(d), 55.00(q), 79.82(d), 113.72(d, intensity for 2CH), 120.52(t), 129.25(d, intensity for 2CH), 132.68(s), 140.62(s), 157.81(s), 170.30(s). |

Preparation of Methyl 3-hydroxy-2-methylidene-propanoate

To a mixture containing 27 ml (25.83 g, 0.30 mmoles of methyl acrylate and 2.5 g (22.29 mmoles) of 1,4-diazabicyclo[2,2,2]-octane (DABCO), formaldehyde was added (generated by pyrolysis of paraformaldehyde at 200° C.) in a nitrogen current for 1 h. The mixture was then left to react for 7 days at room temperature. At the end of that time an extraction was performed with diethyl ether (2×100 ml) and the result was washed with water (2×400 ml). The ether extracts were dried over anhydrous sodium sulphate, filtered and vacuum concentrated, giving 19.5 g (77% yield) of methyl 3-hydroxy-2-methylidene-propanoate in oil form.

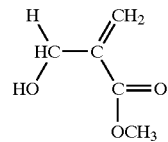

Spectroscopic data.-

| IR $v_{max}$(CHCl$_3$) cm$^{-1}$: | 3428, 3009, 2953, 1718, 1636, 1513, 1439, 1309, 1272, 1159, 1057, 953, 819. |
|---|---|
| EM m/z (rel. int.): | 115[M$^+$-1] (2), 101[M-15]$^+$ (3), 98[M-18]$^+$ (2), 85[M-OCH$_3$]$^+$ (89), 84[M-CH$_3$OH]$^+$ (73), 83[M-15-18]$^+$ (69), 61(12), 55(100). |
| $^1$H RMN (δ, CDCl$_3$): | 3.68(s, 3H, CH$_3$O), 4.22(s, 2H, CH$_2$O), 5.78(s, 1H, CH$_2$=C—), 6.17(s, 1H, CH$_2$=C—). |
| $^{13}$C RMN (δ, CDCl$_3$): | 51.82(q), 61.69(t), 125.50(t), 139.39(s), 166.77(s). |

Preparation of Methyl 2-bromomethyl-2-propenoate

To a solution of N-bromosuccinimide (5.17 g, 26.8 mmoles) in dry dichloromethane (40 ml) were added dimethyl sulphide (4 ml) in dichloromethane (50 ml), drop by drop with stirring at 0° C. for 10 min. To the resulting mixture was added methyl 3-hydroxy-2-metylidene-propanoate (3.15 g, 31.50 mmoles) dissolved in dichloromethane (40 ml), leaving it for 24 hours at room temperature. At the end of that time, it was poured into an aqueous solution of sodium chloride and ice. An extraction was performed with diethyl ether (3×100 ml), and the result was washed with water and dried over anhydrous sodium sulphate. Following vacuum concentration, 4.33 g of a yellow oil was obtained (89% yield) of methyl 2-bromomethyl-2-propenoate.

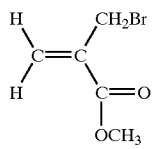

Spectroscopic data.-

| | |
|---|---|
| IR $\upsilon_{max}$ (CHCl$_3$) cm$^{-1}$: | 2997, 2954, 2835, 1736, 1612, 1584, 1513, 1437, 1299, 1248, 1176, 1128, 1035, 960, 825, 772. |
| EM m/z (rel. int.): | 181, 179[M$^+$] (22), 164[M-15]$^+$ (20), 1488[M-OCH$_3$]$^+$(5), 121[M-CO$_2$CH$_3$]$^+$ (93), 85[M-CH$_2$Br]$^+$ (13), 61(100). |
| $^1$H RMN (δ, CDCl$_3$): | 3.76(s wide, 3H, CH$_3$O), 4.07(m, 2H, CH$_2$Br), 5.90(s wide, 1H, HC=C), 6.25(s wide, 1H, HC=C). |
| $^{13}$C RMN (δ, CDCl$_3$): | 33.95(t), 53.59(q), 129.19(19 (t), 137.27(s), 168.20(s). |

Preparation of 5-[2-(4-methoxyphenyl)-ethyl]-3-methylene-dihydrofuran-2-one

To a suspension formed from metallic tin (730 mg, 6.15 mmoles), diethyl ether (12.5 ml) and water (3.1 ml) were added 1.10 g (6.15 mmoles) of methyl 2-bromomethyl-2-propenoate and 1.11 g (6.77 mmoles) of 3-(4-methoxyphenyl) propanal, with catalytic quantities of acetic acid. The mixture was kept warm at 50° C. with stirring for 9 hours. At the end of this time it was poured into water (200 ml) and an extraction was performed with diethyl ether (3×100 ml). The result was dried over anhydrous sodium sulphate and vacuum concentrated, giving an oil 780 mg (70% yield) of 5-[2-(4-methoxyphenyl)-ethyl]-3-metylene-dihydrofuran-2-one [(I), R=CH$_3$; R$_1$=H].

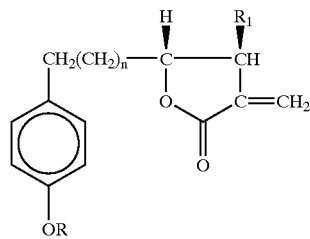

Spectroscopic data.-

| | |
|---|---|
| IR $\upsilon_{max}$ (CHCl$_3$)cm$^{-1}$: | 2996, 2926, 2854, 1760, 1665, 1612, 1584, 1513, 1464, 1398, 1352, 1300, 1279, 1247, 1178, 1129, 1035, 983, 886. |

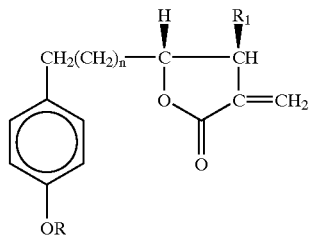

Spectroscopic data.-

| | |
|---|---|
| EM m/z (rel. int.): | 232[M$^+$] (23), 147[M-C$_4$H$_5$O$_2$]$^+$ (31), 135[M-C$_5$H$_5$O$_2$]$^+$ (6), 121[M-C$_6$H$_7$O$_2$]$^+$(100), 91(27), 77(27), 65(13). |
| $^1$H RMN (δ, CDCl$_3$): | 1,96(m, 2H, CH$_2$), 2.70(, 2H, —CH$_2$—), 3.78(s, 3H, O—OCH$_3$), 4.48(m, 1H, —CHO—), 5.62(d, J=5.0 Hz, 1H), 6.22(d, J=5.0 Hz, 1H), 6.83(d, 1=8.5 Hz, 2H), 7.11(d, J=8.5 Hz, 2H). |
| $^{13}$C RMN (δ, CDCl$_3$): | 33.23(t), 33.35(t), 38.13(t), 55.10(q), 76.40(d), 113.61(d, intensity for 2CH), 121(t), 129.23(d, intensity for 2CH), 132.48(s), 157.89(s), 170.18(s). |

BIOLOGICAL ACTIVITY

Biological activities are described of the product described in example 1 (henceforth referred to as "lactone").
Proliferation of Murine Splenocytes. Material and Methods
Test of Lymphocyte Proliferation
Materials

| Processing of the spleen: | |
|---|---|
| Fine curved forceps | Broad flat forceps |
| Separator forceps | Fine scissors |
| Plastic Petri dishes of 60 × 15 mm (FLOW) | Fine wire mesh |
| Pipettes of 5 ml | Pasteur pipettes |
| 10 ml plastic tubes for centrifuging | Filter paper |
| Rubber support for dissection | 70% ethanol |
| Hank's balanced solution (HBSS) (FLOW) | |

Test

Culture medium: DMEM+penicillin 50 UI/ml+streptomycin 50 □g/ml+glutamine 2 mM+10% foetal calf serum (complete medium) (FLOW).

2 Mercaptoethanol (2ME) (Sigma).

Mitogenous controls:
    Concanavalin A (Con A)(SIGMA)
    Phytohaemaglutinin (PHA)(SIGMA)
    Pokeweed (PWM)(SIGMA)
    Lipopolysaccharide 055:B5 (LPS)(SIGMA)

Tripan blue

Dishes with 96 flat-bottom wells (FLOW)

Pipette tips (NUNC)

Tritiated thymidine (AMERSHAM)

Wathman filter papers (Titerted/Skatrom)

Apparatus

Refrigerated centrifuge (BECKMAN)

Liquid scintillation counter LKB 1211 Rack-beta

Optical microscope
Skatron Harvester

Animals

Bal b/c mice were used, male, aged 6–8 weeks (IFFA-CREDO).

Method

Processing of the Spleen

The spleen is extracted under sterile conditions

It is washed with 5 ml of HBSS in a Petri dish

The spleen is laid on wire mesh

It is disintegrated with the aid of broad forceps

The mesh is washed with 5 ml of HBSS and placed in a Petri dish

The tissue pulp is collected with a Pasteur pipette and taken to a sterile centrifuge tube of 10 ml It is washed twice in 10 ml of HBSS and centrifuged at 1,200 r.p.m.

It is resuspended in 11 ml de HBSS

It is left to rest for 5 minutes 10.5 ml are transferred to another centrifuge tube of 10 ml A variables count is conducted with tripan blue The cell suspension is centrifuged at 1,200 r.p.m.

The cell "pellet" is resuspended in complete medium at a concentration of $4 \times 10^6$ cells/ml Test In a dish with 96 flat-bottom wells, seriated dilutions are made of the mitogen problem sample with or without "lactone" in a volume of 10 µl in complete medium to which $5 \times 10^5$ M 2ME have been added. All the determinations are made in triplicate.

100 µl of the cell suspension are then added, leaving a final volume of 200 µl.

The dish is incubated in a stove at 37° C., 5% $CO_2$ for 66 h.

Following that incubation period, 1 µCi of tritiated thymidine is added to each well.

The dish is again incubated for 6 h.

Once that new incubation period has ended, the dish is processed in a Skatron Harvester, using special Wathman filter paper for this.

The filter is dried in air.

The filters are distributed in β counter tubes to which have been added 2 ml of scintillation liquid.

Each tube is introduced into a vial of 12 ml.

The cpm are determined in a liquid scintillation counter.

Controls

Negative control: cells in the presence of complete culture medium.

Positive control: cells in the presence of some mitogen.

Results

These are expressed as:

Arithmetic mean of cpm±standard deviation (1)

$$\text{Stimulation index} = \frac{\text{mean cpm of sample}}{\text{mean cpm of control medium}} \quad (2)$$

The statistical significance is determined by the Student t method.

Tests on Murine Cells Results

A study is first made of the "lactone" effect per se in relation to possible proliferative effects on murine splenocytes. No effect is found in the range 100–0.75 µg/ml (the sample was dissolved in DMSO at 40.0 mg/ml). Nor was are cytotoxicity effects found in the stated ranges.

TABLE 1

Proliferative response of murine splenocytes following 72 h of incubation.
Proliferation of murine splenocytes
Mitogen (cpm ± DS)

| Lactone µg/ml | Con A 2.5 µg/ml | PHA 50 µg/ml | a CD3 20 µg/ml | LPS 10 µg/ml |
|---|---|---|---|---|
| 100 | 147 ± 10 | 19,500 ± 2,000 | 285 ± 20 | 614 ± 35 |
| 50 | 190 ± 10 | 19,000 ± 1,800 | 1,235 ± 200 | 2,700 ± 120 |
| 25 | 244 ± 15 | 21,000 ± 2,000 | 5,600 ± 300 | 3,200 ± 400 |
| 12 | 370 ± 20 | | | |
| 6 | 78,200 ± 725 | | | |
| 3 | 92,600 ± 100 | | | |
| 1.5 | 150,400 ± 12,500 | | | |
| 0.75 | 131,523 ± 10,000 | | | |
| 0 | 150,000 ± 15,000 | 20,000 ± 2,000 | 40,000 ± 4,000 | 30,000 ± 1,600 |

Nevertheless, the lactone clearly demonstrated its capacity for inhibiting proliferation induced by various mitogenic agents: ConA, antiCD$_3$ and LPS, but not that induced by PHA.

The results are summarised in the following tables (the cpm are stated following a pulse of tritiated thymidine. The samples of splenocytes were cultivated for 72 h in the presence of mitogen and lactone at the stated concentrations).

The results indicate the capacity of lactone to specifically inhibit some action signals and not others while in the studies conducted on murine splenocytes, it is seen how the action indicated by the lectin of *Phaseulis vulgaris* (PHA) is not inhibited.

Tests on Human Peripheral Blood Mononuclear Cells Material and Methods:

In order to study more deeply the effects of lactone on cell proliferation, we checked whether the effects described in the above section on cells of murine origin were specific to the cell type and the species or whether, on the other hand, these effects were xeno-independent. For this, we purified human peripheral blood mononuclear cells from healthy controls and we proceeded to study the possible effects of inhibition on the proliferative activity of peripheral blood mononuclear cells (CMSP) from humans, induced by different mitogenic agents acting alone and/or in costimulation with other mitogens and in the presence or absence of recombinant human interleukin 2 (rhIL-2).

Test on Lymphocyte Proliferation

Materials

Apparatus

Air pump for pipetting, Pipetus (Flow Lab., Germany).

Neubauer counting chamber (Saaringia, Germany).

Gelaire TC 48 vertical laminar flow chamber (Flows labs., Germany).

GPR refrigerated centrifuge (Beckman, United Kingdom).

SKATRON AS culture collector (Flow Lab. Lierbayen, Norway).

–30° C. freezer (Selecta, Tarrasa, Spain).

–70° C. freezer (Selecta, Tarrasa, Spain).

Beta counter. Betamatic (Kontron).
Eppendorf multipipette 4780 (Hamburg, Germany).
$CO_2$ culture stove Napco digital 6100 (National Appliance Co., Portland, USA).
Sterile filters of 22 µm Millex-GS (Millipore, Molshein, France).
Olympus CHS-2 microscope (Olympus, Tokyo, Japan).
Glass pipettes of 1, 5 and 10 ml, sterile.
Piptman P Adjustable volume pipettes of 20, 200, 1000 and 5000 µl (Gilson, France).
Sterile dishes with 96 flat-bottom wells (Costar, Cambridge, Mass., USA).
Glass slides and cover slips (Hirschman, Germany).
Virgin propylene tips, sterile (Daslab, Madrid, Spain).
Eppendorf sterile tips (Hamburg, Germany).
Sterile plastic tubes of 5, 10, 15 and 50 ml (Daslab, Madrid, Spain).
Non-sterile plastic tubes of 3 ml (Indubages, S. A., Manresa, Spain).

Test

Tripan blue (Flucke A G., Buchs S G., Germany).
Heparin Leo (Lab. Leo, Madrid, Spain).
Lymphoprep (Ficoll-Hypaque) (Nyegaard Co, Oslo, Norway).
Physiological saline solution (PSS) Simple chlorated apiroserum (Ibys, Madrid, Spain).
Opticint "hisafe" scintillation solution (FSA, Leics, United Kingdom).
Foetal calf serum (FCS) (Gibco, Grand Island, N.Y., USA).
Tritium methyl-$^3$H thymidine. Specific activity 1 µCi/ml. (Amersham inter., United Kingdom).
Mitogens: Phytohaemaglutinin M (PHA) (Difco Lab., Detroit, Mich., USA), Concanavalin A (Con A, 2 µg/ml, Sigma Chemical Co., Mich., USA), Immobilised anti-CD3 (OKT3, 5 µg/ml, Ortho-mune, Orthodiagnostic System) and rhIL-2 (100 IU/ml, Hoffman-La Roche, N.J., USA).

All the reagents included in these tests were diluted in RPMI 1640 culture medium (Whitaker Bioproducts, Walkersville, USA) supplemented with 10% of decomplemented foetal calf serum (Biochrom K G, Berlin), L-glutamin (2 mM, Biochrom K G), Hepes (25 mM, Biochrom K G) and antibiotic (1% penicillin streptomycin, Difco Lab, Detroit, Mich., USA).

Also, all the mitogens were optimised in a dose response way in order to obtaining the maximum proliferative response after 5 days of culture.

Method

Processing of the Samples

Venous blood: The CMSP were obtained from venous blood extracted by antecubital venous puncture. 50 ml of blood were extracted to which were added 50 U of calcic heparin and the mixture was diluted 1/1 (vol/vol) with PSS.

Human mononucleated cells: In order to isolate the CMSP they were proceeded to be separated from the rest of the blood components by means of the formation of a density gradient on Ficoll. The cells thus obtained are resuspended in PSS and centrifuged at 400×g for 10 minutes (washing process) and then resuspended in PSS. This operation is repeated three times. In the last of them, PSS is replaced with complete medium.

In all the cell suspensions a determination was made of the cell concentration and the viability by means of dilution with 0.1% Tripan Blue and microscope counting in a Neubauer chamber. The percentage of live cells was established by the exclusion capacity of the colorant.

General culture conditions: All cell cultures were developed under conditions of sterility in a vertical laminar flow chamber, using single-use sterile materials or materials sterilised in an autoclave or with ethylene oxide. The cultures were conserved in a stove kept at a temperature of 37° C., in an atmosphere with 5% $CO_2$ and relative humidity of 95%. In the various experiments performed, the purified CMSP cell preparations were incubated in sterile dishes with 96 wells at concentrations of 5×10$^4$ cells/well (200 µl) in the presence of different concentrations of different mitogens for 5 days.

Test

The method used for quantifying the cell proliferation was analysis of the incorporation of $^3$H-thymidine ($^3$H-T) into DNA synthesised de novo, detecting the emission of β radiation from the dry extracts of cell cultures to which the tritiated base had been added before its finalisation and collection. The synthesis of DNA was done in triplicate on sterile dishes with 96 flat-bottom wells.

From 20 to 24 hour prior to terminating the cell culture, 1 µCi of $^3$H-T was added to each well containing medium; the cultures were gathered by suction through a glass filter, using a Skatron culture collector for this.

The synthesis of DNA has been expressed in counts per minute (cpm). Each test was conducted in triplicate, with those data having a variability greater than 10% compared to the mean of the triplicate being rejected, since they could indicate a technical error or contamination in the culture. The cultures were carried out at a constant cell volume per well, as well as at a constant volume of 200 µl.

Controls

Negative Control: Cells in the Presence of Complete Culture Medium

Positive Control: Stimulation of Cells without the Presence of Lactone

Tests on Human Peripheral Blood Mononuclear Cells.

Results

The effect was studied of inhibition on the mitogenic activity of human lymphocytes, induced by different mitogenic agents, and of cell activation, acting alone and/or in combination (Table 2).

The spontaneous blastogen response of the CMSP falls by 50% if 0.66 µg/ml of lactone are added to the culture.

The blastogen response induced in CMSP due to phytohaemaglutinin M (PHA) falls by 50% if 0.25 µg/ml of lactone are added to the culture.

The blastogen response induced in CMSP by Concavalin A (Con A) falls by 50% if 0.5 µg/ml of lactone are added to the culture.

The blastogen response induced in CMSP by immobilised anti-CD3 (aCD3), falls by 50% if 0.06 µg/ml of lactone are added to the culture.

The blastogen response induced in CMSP by aCD3+PHA falls by 50% if 0.24 µg/ml of lactone are added to the culture.

The blastogen response induced in CMSP by aCD3+Con A falls by 50% if 0.21 µg/ml of lactone are added to the culture.

TABLE 2

Proliferative response of peripheral blood mononuclear cells. Proliferation of human peripheral blood mononuclear cells Mitogens (cpm ± DS)

| Lactone μg/ml | Medium | PHA 10 μg/ml | Con A 2 μg/ml | aCD3 5 μg/ml | aCD3 + PHA | aCD3 + Con A |
|---|---|---|---|---|---|---|
| 100 | 104 ± 26 | 1086 ± 308 | 204 ± 43 | 39 ± 10 | 13 ± 4 | 8 ± 6 |
| 10 | 72 ± 72 | 71 ± 14 | 48 ± 7 | 119 ± 7 | 23 ± 7 | 11 ± 1 |
| 1 | 1805 ± 1870 | 25118 ± 6642 | 13294 ± 3395 | 1286 ± 255 | 8689 ± 5361 | 829 ± 484 |
| 0.01 | 2867 ± 1527 | 71092 ± 3555 | 55503 ± 9023 | 40378 ± 219 | 67011 ± 8270 | 93139 ± 3070 |
| 0.0001 | 3175 ± 1574 | 76612 ± 15020 | 75329 ± 9144 | 44721 ± 4082 | 105395 ± 375 | 115090 ± 4133 |
| 0 | 2064 ± 39 | 77189 ± 686 | 73639 ± 9993 | 34088 ± 9498 | 95158 ± 7752 | 87804 ± 14148 |

Afterwards, a study is made of the effect of inhibition on the mitogenic activity in human lymphocytes, induced by different mitogenic agents, and of cell activation, acting alone and/or in combination following the addition of exogen interleukin 2 (Table 3).

The blastogen response induced in CMSP by rhIL-2 falls by 50% if 0.26 μg/ml of lactone are added to the culture.

The blastogen response induced in CMSP by PHA+rhIL-2 falls by 50% if 0.29 μg/ml of lactone are added to the culture.

The blastogen response induced in CMSP by Con A+rhIL-2 falls by 50% if 0.27 μg/ml of lactone are added to the culture.

The blastogen response induced in CMSP by immobilised aCD3+rhIL-2 falls by 50% if 0.24 μg/ml of lactone are added to the culture.

The blastogen response induced in CMSP by immobilised aCD3+PHA+rhIL-2 falls by 50% if 0.26 μg/ml of lactone are added to the culture.

The blastogen response induced in CMSP by immobilised aCD3+Con A+rhIL-2 falls by 50% if 0.25 μg/ml of lactone are added to the culture.

TABLE 3

Proliferative response of peripheral blood mononuclear cells in the presence of rhIL-2. Proliferation of human peripheral blood mononuclear cells Mitogens in the presence of rhIL-2 (100 UI/ml) (cpm ± DS)

| Lactone μg/ml | Medium | PHA 10 μg/ml | Con A 2 μg/ml | aCD3 5 μg/ml | aCD3 + PHA | aCD3 + Con A |
|---|---|---|---|---|---|---|
| 100 | 918 ± 1 | 892 ± 199 | 532 ± 109 | 400 ± 44 | 286 ± 10 | 237 ± 109 |
| 10 | 866 ± 66 | 579 ± 1033 | 611 ± 75 | 489 ± 25 | 304 ± 35 | 164 ± 65 |
| 1 | 9548 ± 808 | 110507 ± 698 | 71210 ± 5211 | 36280 ± 77 | 88220 ± 3174 | 66429 ± 9241 |
| 0.01 | 42568 ± 8631 | 106754 ± 698 | 54196 ± 80 | 39771 ± 3258 | 94165 ± 15647 | 130949 ± 16623 |
| 0.0001 | 56451 ± 4965 | 130524 ± 8929 | 96972 ± 18274 | 87091 ± 7078 | 133621 ± 12440 | 154981 ± 15723 |
| 0 | 45902 ± 7074 | 123500 ± 3682 | 118716 ± 4052 | 112214 ± 15621 | 147591 ± 16848 | 146999 ± 12727 |

TABLE 4

Methodological control over the observed effect of lactone towards different mitogens. Proliferation of human peripheral blood mononuclear cells Mitogens (cpm ± DS)

| Lactone μg/ml | Medium | PHA 10 μg/ml | PHA + rhIL-2 |
|---|---|---|---|
| 100 | 47 ± 5 | 906 ± 251 | 341 ± 21 |
| 0.25 | 283 ± 9 | 60428 ± 5820 | 144693 ± 9470 |
| 0 | 318 ± 37 | 113032 ± 1649 | 158221 ± 6856 |

Stability Studies

Finally, we analyse the stability over time of the product dissolved in dimethylsulphoxide (DMSO) by means of new experiments in which, once again, the antiproliferative biological activity of lactone is demonstrated (Table 4).

The sample remains for one year at room temperature and at a concentration of 40.0 mg/ml in DMSO.

What is claimed is:

1. A lactone compound, characterised in that it has a formula selected from the group consisting of:

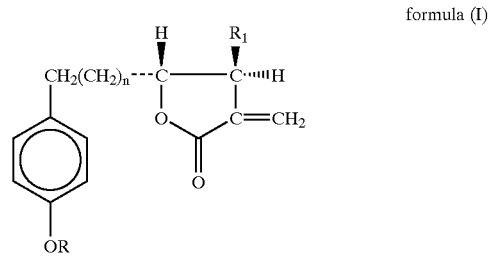

formula (I)

wherein n can take the values 1,2,3; R can be H or $CH_3$ and $R_1$ can be $CH_3$ or H and formula (Ia)

wherein n can take the values 1,2,3; R can be H or $CH_3$ and $R_1$ can be $CH_3$ or H.

* * * * *

UNITED STATES PATENT AND TRADEMARK OFFICE
CERTIFICATE OF CORRECTION

PATENT NO. : 6,818,780 B2 Page 1 of 1
APPLICATION NO. : 10/251914
DATED : November 16, 2004
INVENTOR(S) : Jamie Bermejo Barrera et al.

It is certified that error appears in the above-identified patent and that said Letters Patent is hereby corrected as shown below:

Title page, item [73]

Please add the following Assignees:

--Investigatión Y Medicina, S.L.-- and --Saetabis Bio Consulting--

Signed and Sealed this

Tenth Day of July, 2007

JON W. DUDAS
*Director of the United States Patent and Trademark Office*